United States Patent [19]

Sehnem

[11] 4,452,992

[45] Jun. 5, 1984

[54] PROCESS FOR THE PRODUCTION OF ETHOXYCARBONYLMETHYL 5-(2,6-DICHLORO-4-TRIFLUORO-METHYL-PHENOXY)-2-NITRO-α-PHENOXY-PROPIONATE

[75] Inventor: Hans P. Sehnem, Wuppertal, Fed. Rep. of Germany

[73] Assignee: Bayer Aktiengesellschaft, Leverkusen, Fed. Rep. of Germany

[21] Appl. No.: 457,774

[22] Filed: Jan. 13, 1983

[51] Int. Cl.³ .............................................. C07C 79/46
[52] U.S. Cl. ...................................................... 560/21
[58] Field of Search ............................................. 560/21

[56] References Cited

U.S. PATENT DOCUMENTS 4,063,929 12/1977 Bayer et al. ............................ 71/115
4,221,581 9/1980 Rohr et al. ............................... 71/70

FOREIGN PATENT DOCUMENTS 20052 10/1980 European Pat. Off. .............. 560/21

*Primary Examiner*—Paul J. Killos
*Attorney, Agent, or Firm*—Sprung, Horn, Kramer & Woods

[57] ABSTRACT

A novel process for the preparation of ethoxycarbonyl-methyl 5-(2,6-dichloro-4-trifluoromethyl-phenoxy-2-nitro-α-phenoxy-propionate of the formula

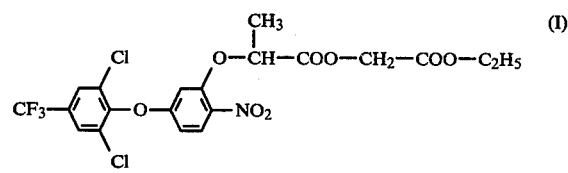

by reacting ethoxycarbonylmethyl 3-(2,6-dichloro-4-trifluoromethyl-phenoxy)-α-phenoxy-propionate of the formula

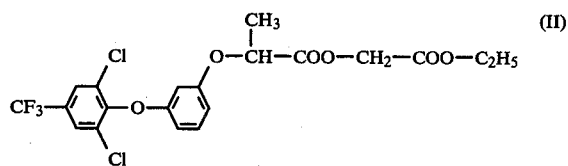

with nitric acid in the presence of sulphuric acid and in the presence of 1,2-dichloroethane at a temperature between $-20°$ C. and $+150°$ C.

5 Claims, No Drawings

PROCESS FOR THE PRODUCTION OF ETHOXYCARBONYLMETHYL 5-(2,6-DICHLORO-4-TRIFLUORO-METHYL-PHENOXY)-2-NITRO-α-PHENOXY-PROPIONATE

This invention relates to a novel process for the production of the known ethoxycarbonylmethyl 5-(2,6-dichloro-4-trifluoromethyl-phenoxy)-2-nitro-α-phenoxypropionate, which compound exhibits herbicidal properties.

It has already been disclosed that the ethoxycarbonylmethyl 5-(2,6-dichloro-4-trifluoromethylphenoxy)-2-nitro-α-phenoxy-propionate can be prepared by reacting 5-(2,6-dichloro-4-trifluoromethyl-phenoxy)-2-nitro-α-phenoxy-propionyl chloride with ethyl hydroxy-acetate in the presence of an acid-binding agent (see DE-OS (German Published Specification) No. 2,906,087). The decisive disadvantage of this process consists in the fact that the desired product is obtained in yields, which are too low for practical purposes.

The present invention now provides a process for the production of ethoxycarbonylmethyl 5-(2,6-dichloro-4-trifluoromethyl-phenoxy)-2-nitro-α-phenoxy-propionate of the formula

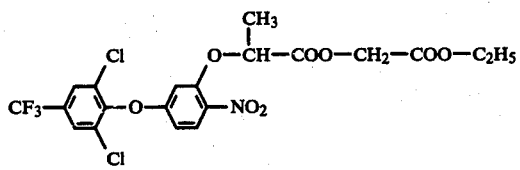

which comprises reacting ethoxycarbonylmethyl 3-(2,6-dichloro-4-trifluoromethyl-phenoxy)-α-phenoxy-propionate of the formula

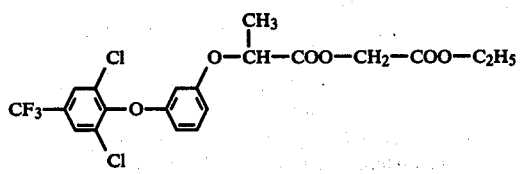

with nitric acid in the presence of sulphuric acid and in the presence of 1,2-dichloroethane at a temperature between −20° C. and +150° C.

It must be described as decidedly surprising that ethoxycarbonylmethyl 5-(2,6-dichloro-4-trifluoromethyl-phenoxy)-2-nitro-α-phenoxy-propionate of the formula (I) is obtained by the process according to the invention in an excellent purity and extremely high yields, since in the nitration of the methoxycarbonylmethyl 3-(2,6-dichloro-4-trifluoromethyl-phenoxy)-α-phenoxy-propionate the corresponding nitrated methyl ester is only formed in a relatively low yield. Such a marked difference in the course of the reaction of the nitration of homologous diphenyl ether derivatives could not be expected on basis of the prior art teaching.

The process according to the invention has a number of advantages. Thus, the substances which are needed as starting materials are both obtainable in large amounts in a simple manner and also can be manipulated on an industrial scale without problems. Furthermore, the expenditure on equipment necessary for carrying out the process according to the invention is slight and the working up after completion of reaction is not difficult. Particularly, however, the ethoxycarbonylmethyl 5-(2,6-dichloro-4-trifluoromethylphenoxy)-2-nitro-α-phenoxy-propionate is obtained by the process according to the invention in a substantially higher yield than according to the hitherto known synthesis. Thus, the process according to the invention represents a valuable enlargement of industrial possibilities.

The course of the process according to the present invention is illustrated by the following reaction scheme:

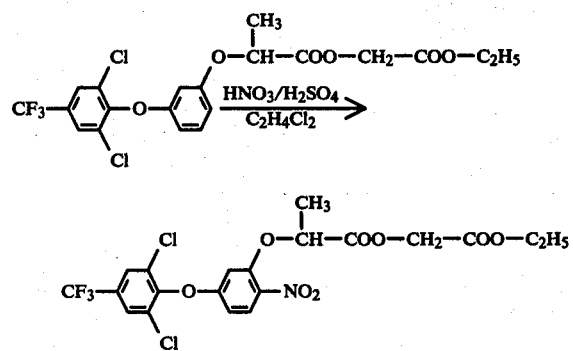

The ethoxycarbonylmethyl 3-(2,6-dichloro-4-trifluoromethyl-phenoxy)-α-phenoxy-propionate to be used as starting material in the process according to the invention is already known (see DE-OS (German Published Specification) No. 2,805,981). The respective compound can be prepared, for example, by reacting 3-(2,6-dichloro- 4-trifluoromethyl-phenoxy)-phenol of the formula

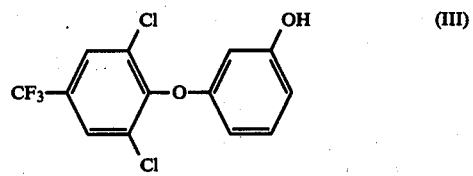

with ethoxycarbonylmethyl α-bromo-propionate of the formula

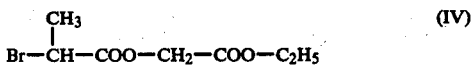

in the presence of an acid-binding agent (such as potassium carbonate), and in the presence of an inert diluent (such as acetone), at a temperature between 40° and 70° C. The working up is carried out by customary methods.

In the process according to the invention, the nitration is carried out with a mixture of nitric acid and sulphuric acid. Fuming nitric acid and concentrated or at least highly concentrated sulphuric acid are preferably employed. Particularly useful is a mixture of nitric acid of a concentration of 96% and of sulphuric acid of a concentration of 96%.

1,2-Dicloroethane is employed as a diluent in the reaction for the process according to the invention. However, it is also possible to substitute the 1,2-dichloroethane partially or completely by other chlorinated hydrocarbons, such as carbon tetrachloride or chloroform.

The reaction temperature for the process according to the invention can be varied within a certain range. The reaction is preferably carried out at a temperature between −15° C. and +30° C., especially between −10° C. and +10° C.

The process according to the invention is generally carried out under normal pressure.

In order to carry out the process according to the invention, 1 to 10 moles, preferably 2.5 to 7.5 moles of nitric acid and 0.5 to 10 moles, preferably 1 to 5 moles of sulphuric acid are are employed for 1 mol of ethoxycarbonylmethyl 3-(2,6-dichloro-4-trifluoromethyl-phenoxy)-α-phenoxy-propionate. In detail, the process according to the invention is carried out by a procedure in which the mixture of nitric acid and sulphuric acid to be used for the nitration is added dropwise, whilst stirring and cooling, to a solution of the compound of the formula (II) in 1,2-dichloroethane. The isolation of the reaction product is carried out by customary methods. In general, the procedure is such that the reaction mixture is mixed with water, and the mixture produced thereby is extracted several times, with an organic solvent, such as 1,2-dichloroethane. Subsequently, the combined organic phases are washed with water and then the solvent is evaporated under reduced pressure. The remaining oily residue is converted to the solid state by treatment with a suitable organic solvent (such as isopropanol or cyclohexane) and, if appropriate, recrystallization is carried out, for example from an alcohol (such as isopropanol) or from cyclohexane or even from water.

The process according to the invention can be carried out continuously or in a batchwise manner.

The exthoxycarbonylmethyl 5-(2,6-dichloro-4-trifluoromethyl-phenoxy)-2- nitro-α-phenoxy-propionate which can be prepared by the process according to the invention has herbicidal properties (see DE-OS (German Published Specification) 2,906,087). The compound is particularly suitable for selective weed control.

The process according to the invention and its superiority compared to the hitherto known process for the preparation of the compound of the formula (I) as well as the unexpected course of the process according to the invention compared to the corresponding nitration of the methoxycarbonylmethyl 3-(2,6-dichloro-4- trifluoromethyl-phenoxy)-α-phenoxy propionate are illustrated by the following Examples.

PREPARATIVE EXAMPLES

A. Examples according to the invention

EXAMPLE 1

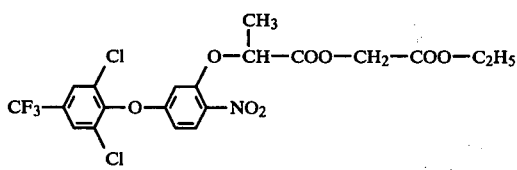

A mixture of 64 g (0.625 moles) of 96% strength sulphuric acid and 82 g (1.25 moles) of 96% strength nitric acid was added dropwise, whilst stirring, to a solution of 120.3 g (0.25 moles) of ethoxycarbonylmethyl 3-(2,6dichloro-4-trifluoromethyl-phenoxy)-α-phenoxy-propionate in 1000 ml of 1,2-dichloroethane at a temperature between -10° C. and -5° C.

After having completed the addition the reaction mixture was stirred for a further 60 minutes at -10° C. to 5° C. The reaction mixture was subsequently mixed with 350 ml of water, whilst cooling, and the phases were separated. The aqueous phase was extracted once with 200 ml of 1,2-dichloroethane. The combined organic phases were washed with 200 ml of water and then were concentrated by evaporating the solvent under reduced pressure. The remaining red-brown, highly viscous oil crystallised after treatment with isopropanol. The solid product was filtered off and dried. 120.2 g (91,4% of theory) of ethoxycarbonylmethyl 5-(2,6-dichloro-4trifluoromethyl-phenoxy)-2-nitro-α-phenoxy-propionate were obtained in this manner in the form of a crystalline solid product of melting point 74°–75° C.

EXAMPLE 2

Preparation of the starting material of the formula

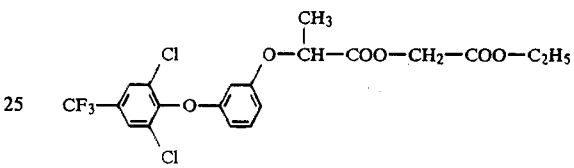

63 g (0.2625 mol) of ethoxycarbonylmethyl α-bromo-propionate were added dropwise, with stirring, to a mixture of 80.8 g (0.25 mol) of 3-(2,6-dichloro-4-trifluoromethyl-phenoxy)-phenol, 350 ml of acetone and 41.4 g (0.3 mol) of potassium carbonate at 50° to 60° C. The reaction mixture was subsequently stirred a further 7 hours at 50° to 60° C. The reaction mixture was then worked up by adding 500 ml of water and 500 ml of toluene, separating the phases, extracting the aqueous phase once with 200 ml of toluene, washing the combined organic phases once with 200 ml of 5% strength aqueous sodium hydroxide solution and once with 200 ml of water and, after drying over sodium sulphate, distilling off the solvent under reduced pressure. In this manner, 90.8 g (75.5% of theory) of ethoxycarbonylmethyl 3-(2,6-dichloro-4-trifluoromethylphenoxy-α-phenoxy-propionate were obtained in the form of a yellow oil.

B. COMPARISON EXAMPLES

EXAMPLE 3

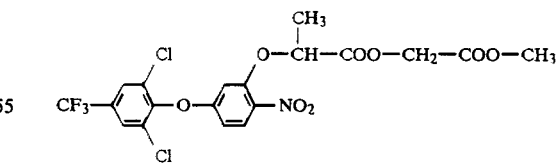

A mixture of 3.3 g (0.05 moles) of 96% strength nitric acid and 2.6 g (0.025 moles) of 96% strength sulphuric acid was added dropwise, whilst stirring, to a solution of 4.7 g (0.01 mol) of methoxycarbonylmethyl 3-(2,6-dichloro-4-trifluoromethyl-phenoxy)-α-phenoxy-propionate in 50 ml of 1,2-dichloroethane at a temperature between −10° C. and −5° C. After having completed the addition, the reaction mixture was stirred for a further 3 hours at −10° C. to −5° C. The reaction mixture was subsequently mixed with 20 ml of water, whilst cooling, and the phases were separated. The aqueous phase was extracted once with 25 ml of 1,2-dicloroethane. The combined organic phases were washed consecutively with 25 ml of saturated aqueous sodium bicarbonate solution and with 25 ml of water and were then concentrated by evaporating the solvent under reduced pressure. There were obtained 5.4 g of a red-brown, highly-viscous oil, which, according to its gas chromatogram, contained the methoxy- carbonyl-methyl 5-(2,6-dichloro-4-trifluoromethyl-phenoxy) -2-nitro-α-phenoxy-propionate in an amount of 56.9%. Accordingly, the yield of this substance was calculated to be 60.1% of theory.

EXAMPLE 4

Preparation of the compound of the formula

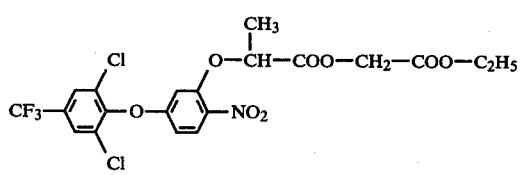

by the process according to DE-OS (German Published Specification No.) 2,906,087 .

A solution of 15 g of 5-(2,6-dichloro-4-trifluoromethyl- phenoxy)-2-nitro-α-phenoxypropionyl chloride in 30 ml of toluene was added dropwise to a solution of 3.7 g of ethyl hydroxyacetate and 4 g of triethylamine in 70 ml of toluene cooled to 0° to 5° C. The reaction mixture was stirred at room temperature overnight, diluted with 300 ml of toluene, washed to neutrality, dried, filtered and evaporated. 13.5 g ethoxycarbonylmethyl 5-(2,6-dicloro-4-trifluoromethyl-phenoxy)-2nitro-α- phenoxypropionate were initially obtained in the form of a yellowish oil which then crystallised. Melting point: 75° to 76° C. The yield of pure substance was calculated to be 70.5% of theory.

It will be understood that the specification and examples are illustrative, but not limitative of the present invention and that other embodiments within the spirit and scope of the invention will suggest themselves to those skilled in the art.

What is claimed is:

1. A process for the production of ethoxycarbonylmethyl 5-(2,6-dichloro-4-trifluoromethyl-phenoxy)-2-nitro-α-phenoxy-propionate of the formula

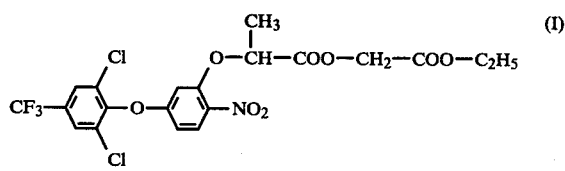

which process comprises reacting exthoxycarbonylmethyl 3-(2,6-dichloro-4-trifluoromethyl-phenoxy)-α-phenoxypropionate of the formula

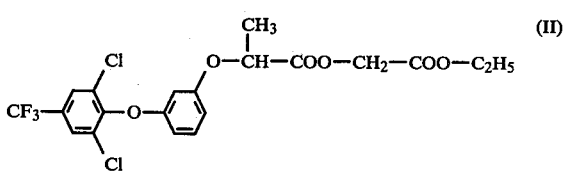

is reacted with nitric acid in the presence of sulphuric acid and in the presence of 1,2-dichloroethane at a temperature between −20° C. and +50° C.

2. A process according to claim 1, wherein the nitric acid employed is in the form of fuming nitric acid.

3. A process according to claim 1, wherein the sulphuric acid employed is in the form of concentrated or at least highly concentrated form.

4. A process according to claim 1, wherein the reaction is carried out at a temperature between −15° C. and +30° C.

5. A process according to claim 1, wherein 1 to 10 moles of nitric acid and 0.5 to 10 moles of sulphuric acid are employed per 1 mol of exhoxycarbonylmethyl 3-(2,6-dichloro-4-trifluoromethyl-phenoxy)-α-phenoxypropionate of the formula (II).

* * * * *

UNITED STATES PATENT AND TRADEMARK OFFICE
CERTIFICATE OF CORRECTION

PATENT NO. : 4,452,992
DATED : June 5, 1984
INVENTOR(S) : Hans P. Sehnem

It is certified that error appears in the above-identified patent and that said Letters Patent is hereby corrected as shown below:

| | |
|---|---|
| Col. 1, line 34 | Before "comprises" insert --process-- |
| Col. 1, line 48 | After "that" insert --the-- |
| Col. 3, line 66 | After "2,6" insert -- - -- |
| Col. 4, line 3 | Delete "5°C." and substitute -- -5°C.-- |
| Col. 4, line 13 | After "dichloro-4" insert -- - -- |
| Col. 5, lines 2, 3 | Delete "dicloroethane" and substitute --dichloroethane-- |
| Col. 5, line 36 | After "-2" insert -- - -- |
| Col. 6, line 40 | Delete "exhoxycarbonylmethyl" and substitute --ethoxycarbonylmethyl-- |
| Col. 5, line 36 | Delete "dicloro" and substitute --dichloro-- |

Signed and Sealed this

Twenty-fifth Day of December 1984

[SEAL]

Attest:

GERALD J. MOSSINGHOFF

Attesting Officer    Commissioner of Patents and Trademarks